US008394821B2

(12) United States Patent
Ono (10) Patent No.: US 8,394,821 B2
(45) Date of Patent: Mar. 12, 2013

(54) ACTIVATED BLOOD COAGULATION FACTOR INHIBITOR

(75) Inventor: Makoto Ono, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/181,596

(22) Filed: Jul. 13, 2011

(65) Prior Publication Data

US 2011/0312991 A1    Dec. 22, 2011

Related U.S. Application Data

(63) Continuation of application No. PCT/JP2010/050128, filed on Jan. 8, 2010.

(30) Foreign Application Priority Data

Jan. 13, 2009   (JP) .................................. 2009-004904

(51) Int. Cl.
*C07D 215/38*   (2006.01)
*A61K 31/04*    (2006.01)

(52) U.S. Cl. ........................................ 514/301; 546/114
(58) Field of Classification Search .................. 546/114; 514/301

See application file for complete search history.

(56) References Cited

U.S. PATENT DOCUMENTS

| | | | |
|---|---|---|---|
| 5,055,600 A | 10/1991 | Wagner | |
| 5,149,855 A | 9/1992 | Sakimae et al. | |
| 5,677,469 A | 10/1997 | van Eikeren et al. | |
| 7,192,968 B2 | 3/2007 | Yoshino et al. | |
| 7,342,014 B2* | 3/2008 | Ohta et al. ................ | 514/252.04 |
| 7,365,205 B2* | 4/2008 | Ohta et al. ................... | 546/256 |
| 7,576,135 B2 | 8/2009 | Ohta et al. | |
| 7,674,904 B2 | 3/2010 | Doshan et al. | |
| 2004/0122063 A1 | 6/2004 | Yoshino et al. | |
| 2005/0020645 A1 | 1/2005 | Ohta et al. | |
| 2005/0119486 A1* | 6/2005 | Ohta et al. ................... | 546/256 |
| 2005/0245565 A1 | 11/2005 | Ohta et al. | |
| 2006/0252837 A1 | 11/2006 | Ohta et al. | |
| 2006/0275357 A1 | 12/2006 | Oomura et al. | |
| 2007/0135476 A1 | 6/2007 | Nagasawa et al. | |
| 2008/0015215 A1 | 1/2008 | Ohta et al. | |
| 2009/0105491 A1 | 4/2009 | Sato et al. | |
| 2009/0192313 A1 | 7/2009 | Nagasawa et al. | |
| 2009/0270446 A1 | 10/2009 | Ohta et al. | |
| 2009/0281074 A1 | 11/2009 | Ohta et al. | |
| 2010/0081685 A1 | 4/2010 | Kojima et al. | |

FOREIGN PATENT DOCUMENTS

| | | |
|---|---|---|
| JP | 4-227629 | 8/1992 |
| JP | 11-180899 | 7/1999 |
| JP | 2000-344735 | 12/2000 |
| JP | 2001-151724 | 6/2001 |
| JP | 2008-542287 | 11/2008 |
| WO | WO 01/74774 | 10/2001 |
| WO | 03000657 | * 1/2003 |
| WO | WO 03/000657 | 1/2003 |
| WO | WO 03/000680 | 1/2003 |
| WO | WO 03/016302 | 2/2003 |
| WO | WO 2004/058715 | 7/2004 |
| WO | WO 2005/047296 | 5/2005 |
| WO | WO 2007/032498 | 3/2007 |
| WO | WO 2008/129846 | 10/2008 |
| WO | WO 2008/156159 | 12/2008 |

OTHER PUBLICATIONS

Serajuddin, Abu, "Salt formation to improve drug solubility", Advanced Drug Delivery Reviews, 59, 2007, pp. 603-616.*
Hcaplus 2003:5928, "Preparation of N, N'-bis (heterocyclediamine derivatives as inhibitors of activated blood coagulation factor X (factor Xa)", Ohta et. al., 2003.*
Blagden et. al., "Crystal engineering of active pharmaceutical ingredients to improve solubility and dissolution rates", Advanced Drug Delivery Reviews, 59, 2007, pp. 617-630.*
PCT International Preliminary Report on Patentability of Int'l App. No. PCT/JP2010/053905 dated Oct. 18, 2011, 5 pages.
International Search Report of Int'l App. No. PCT/JP2010/053905 dated Apr. 21, 2010, 2 pages.
English Translation of PCT Written Opinion of the International Searching Authority of Int'l App. No. PCT/JP2010/053905 dated May 11, 2010, 4 pages.
PCT International Preliminary Report on Patentability of Int'l App. No. PCT/JP2010/053976 dated Oct. 18, 2011, 5 pages.
International Search Report of Int'l App. No. PCT/JP2010/053976 dated Apr. 13, 2010, 2 pages.
English Translation of PCT Written Opinion of the International Searching Authority of Int'l App. No. PCT/JP2010/053976 dated Apr. 13, 2010, 4 pages.
Patani, et al., "Bioisosterism: A rational approach in drug design", *Chem. Rev.* 1996, 3147-3176.
U.S. Appl. No. 13/231,081, filed Sep. 2, 2011, Koutarou Kawanami.
U.S. Appl. No. 13/228,928, filed Sep. 9, 2011, Takeo Koyama.
Dubois, D., et al., "Clinical calorimetry. X. A formula to estimate the approximate surface area if the height and weight be known" *Archives of Internal Medicine*, 17, 863-71 (1916).
Elodi, S., et al., "Optimization of conditions for the catalytic effect of the factor IXa-factor VIII complex: probable role of the complex in the amplification of blood coagulation" *Thrombosis Research*, 15(5-6), 617-29 (1979).
Fujimoto, et al., "Studies on the physical surface area of Japanese: Part 18 calculation formulas in three stages over all age" *Japanese Journal of Hygiene*, vol. 23(5): 443-450 (1968)—(Contains an English Abstract).

(Continued)

*Primary Examiner* — D M Seaman
(74) *Attorney, Agent, or Firm* — Locke Lord LLP (57) ABSTRACT

An object of the present invention is to provide a novel salt form of a compound that exhibits an inhibitory effect on activated blood coagulation factor X, and is useful as a preventive and/or therapeutic drug for thrombotic diseases, and crystals thereof. The present invention provides $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide tartrate and crystals thereof, as a novel salt form of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide and crystals thereof.

12 Claims, 8 Drawing Sheets

OTHER PUBLICATIONS

Furugohri, T., et al., "DU-176b, A potent and orally active factor Xa inhibitor: In vitro and in vivo pharmacological profiles" *Journal of Thrombosis and Haemostasis*, 6(9), 1542-1549 (2008).

Goldberg, SI, et al., "Correlation of configuration and rotatory direction for several 4-substituted cyclohexenes" *Journal of Organic Chemistry*, 31:240-243 (1966).

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" *Blood* 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" *Journal of Clinical Pharmacology*, 49(9), 1125 (2009).

Mendell, J., et al., "Thorough QT/QTC study with edoxaban to evaluate effect of therapeutic and supratherapeutic exposure on QTC interval duration in healthy subjects" *Journal of Clinical pharmacology* 49(9), 1122 (2009).

Mould, D., et al., "A population pharmacokinetic pharmacodynamic and logistic regression analysis of lotrafiban in patients" *Clinical Pharmacology and Therapeutics* 69(4), 210-222 (2001).

Mueck, W., et al., "Population pharmacokinetics and pharmacodynamic of rivaroxaban—an oral, direct factor Xa inhibitor—in patients undergoing major orthopaedic surgery" *Clinical Pharmacokinetics*, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999).

Product Information, Clexane® and Clexane® Forte, Clexane® PI MKT, #6178v16, pp. 1-19 (2008).

Ridout, G., et al., "Effect of renal function on edoxaban pharmacokinetics (PK) and on population PK/PK-PD model" *Journal of Clinical Pharmcology* 49(9), 1124 (2009).

Schwartz, HM, et al., "Predicting the Enantiomeric Selectivity of Chymotrypsin. Homologous Series of Ester Substrates" *J. Am. Chem. Soc.*, 100, 5199-5203, (1978).

Sixma JJ, et al., "The ideal anti-thrombotic drug" *Thrombosis research*, 68(6), 507-12 (1992).

Takahashi, H. "3.Warfarin Oto no kojinsa" *Kessen to Junkan*, 14(3), 198-202 (2006) (English Translation Provided).

Tanyeli, C, et al., "Enzyme catalyzed reverse enantiomeric separation of methyl (±)-3-cyclohexene-1-carboxylate" *Tetrahedron: Asymmetry*, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" *Thrombosis and Haemostasis*, 90(6), 1163-1172 (2003).

International Preliminary Report on Patentability, issued in PCT/JP2009/070613, mailed Jul. 5, 2011.

International Search Report, issued in PCT/JP2009/070613, mailed Feb. 16, 2010.

Written Opinion of the International Searching Authority, issued in PCT/JP2009/070613, mailed Jul. 5, 2011.

International Preliminary Report on Patentability, issued in PCT/JP2009/070874, mailed Jul. 5, 2011.

International Search Report, issued in PCT/JP2009/070874, mailed Mar. 23, 2010.

Written Opinion of the International Searching Authority, issued in PCT/JP2009/070874, mailed Jul. 5, 2011.

International Preliminary Report on Patentability, issued in PCT/JP2009/071016, mailed Jul. 5, 2011.

International Search Report, issued in PCT/JP2009/071016, mailed Feb. 16, 2010.

Written Opinion of the International Searching Authority, issued in PCT/JP2009/071016, mailed Jul. 5, 2011.

International Preliminary Report on Patentability, issued in PCT/JP2010/050128, mailed Aug. 16, 2011.

International Search Report, issued in PCT/JP2010/050128, mailed Apr. 6, 2010.

Written Opinion of the International Searching Authority, issued in PCT/JP2010/050128, mailed Aug. 16, 2011.

International Preliminary Report on Patentability, issued in PCT/JP2010/057990, mailed Dec. 12, 2011.

International Search Report, issued in PCT/JP2010/057990, mailed Jun. 8, 2010.

Written Opinion of the International Searching Authority, issued in PCT/JP2010/057990, mailed Dec. 12, 2011.

International Preliminary Report on Patentability, issued in PCT/JP2010/060261, mailed Dec. 20, 2011.

International Search Report, issued in PCT/JP2010/060261, mailed Sep. 21, 2010.

Written Opinion of the International Searching Authority, issued in PCT/JP2010/060261, mailed Dec. 20, 2011.

U.S. Appl. No. 13/157,590, filed Jun. 10, 2011, Koji Sato.
U.S. Appl. No. 13/162,922, filed Jun. 17, 2011, Takeo Koyama.
U.S Appl. No. 13/163,287, filed Jun. 17, 2011, Takashi Abiko.
U.S. Appl. No. 13/273,360, filed Oct. 14, 2011, Toshiharu Yoshino.
U.S. Appl. No. 13/328,847, filed Dec. 16, 2011, Makoto Kamada.

Kozma, D., "CRC Handbook of Optical Resolutions Via Diastereomeric Salt Formation", CRC Press: Washington, DC, Chapters 4, 5, and 6 (2002).

Murakami, "Asymmetric Transformation of a Racemic a-(Phtha 1 imidooxy)arylacetic Ester by a Combination of Preferential Crystallization and Simultaneous Racemization" *Chirality* 5141-48 (1993).

Allan, R., "Synthesis of analogs of GABA. VI. Stereoisomers of cis-3-aminocyclohexanecarboxylic acid" *Australian Journal of Chemistry*, 34(10):2231-36 (Abstract only), 1981.

Chiappe, et al. "Nucleophilic Displacement Reactions in Ionic Liquids: Substrate and Solvent Effect in the Reaction of $NaN_3$ and KCN with Alkyl Halides and Tosylates," *Journal of Organic Chemistry* 68:6710-15 (2003).

Betti, C., et al. "Reactivity of anionic nucleophiles in ionic liquids and molecular solvents," *Tetrahedron* 64:1689 (2008).

U.S. Appl. No. 13/554,610, filed Jul. 20, 2012, Tetsuya Kimura.
U.S. Appl. No. 13/622,783, filed Sep. 19, 2012, Tetsuya Suzuki.

Supplementary European Search Report mailed Jun. 4, 2012 in EP Application No. 09 83 3467, which corresponds to U.S. Appl. No. 13/163,287.

Furugohri, T, et al, "Pharmaceutical Characterization, Antithromboti and Bleeding Effects of DU-176b", Journal of Thrombosis and Haemostasis, 3(supp. 1), Abstract P1110, (2005).

Zafar, UM, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).

Walker, MB, "Understanding the PT-INR Test", obtained from the internet www.vclotacare.com/ptinr.aspx (retrieved Apr. 24, 2012).

Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).

Thomas, M., et al, "Management of Venous Thromboembolism", *Arch Intern Med.*, 163:759-768 (2003).

Turpie, AGG., "Oral, direct factor Xa inhibitors in development for the prevention and treatment of thromboembolic diseases", *Arteriosclerosis, Thrombosis, and Vascular Biology*, 27:1238-1247 (2007).

De Caterina, R, et al. "Anticoagulants in heart disease: current status and perspectives", *European Heart Journal* 28:880-913 (2007).

Dyke, CK., "First experience with direct factor Xa inhibition in patients with stable coronary disease: a pharmacokinetic and pharmacodynamics evaluation", *Circulation.*, 105:2385-2391 (2002).

Iba, T., et al., "Factor Xa-inhibitor (DX-9065a) modulates the leukocyte-endothelial cell interaction in endotoxemic rat", *Shock.*, 17(2):159-162 (2002).

Office of Generic Drugs, "Scoring Configuration of Generic Drug Products", dated Nov. 1, 1995; www.fda.gov/downloads/AboutFDA/

CentersOffices/CDER/ManualofPoliciesProcedures/ucm079779.pdf; accessed Sep. 6, 2012; cited in related U.S. Appl. No. 13/163,287.

International Search Report, issued in related International Application No. PCT/JP2011/055955, mailed May 24, 2011.

Written Opinion of the International Searching Authority, issued in related International Application No. PCT/JP2011/055955, mailed May 24, 2011.

* cited by examiner

ACTIVATED BLOOD COAGULATION FACTOR INHIBITOR

This application is a continuation of International Application No. PCT/JP2010/050128, filed on Jan. 8, 2010, entitled "ACTIVE BLOOD COAGULATION FACTOR INHIBITOR", which claims the benefit of Japanese Patent Application Number JP 2009-004904, filed on Jan. 13, 2009, all of which are hereby incorporated by reference.

FIELD OF THE INVENTION

The present invention relates to a salt of a compound that exhibits an inhibitory effect on activated blood coagulation factor X (FXa), and is useful as a preventive and/or therapeutic drug for thrombotic diseases, and to crystals thereof.

BACKGROUND OF THE INVENTION $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (A) (hereinafter, also referred to as compound A):

[Formula 1]

(A)

exhibits an inhibitory effect on activated blood coagulation factor X, and its usefulness as a preventive and/or therapeutic drug for thrombotic diseases can be expected (Patent Literature 1 to 8). It is known that compound A is obtained as a hydrochloride or a p-toluenesulfonate monohydrate (Patent Literature 1 to 8).

CITATION LIST

Patent Literature

Patent Literature 1: International Publication No. WO 03/000657
Patent Literature 2: International Publication No. WO 03/000680
Patent Literature 3: International Publication No. WO 03/016302
Patent Literature 4: International Publication No. WO 04/058715
Patent Literature 5: International Publication No. WO 05/047296
Patent Literature 6: International Publication No. WO 07/032498
Patent Literature 7: International Publication No. WO 08/129846
Patent Literature 8: International Publication No. WO 08/156159

SUMMARY OF INVENTION

Technical Problem

It has been demanded to develop a novel salt form of a compound A, which is preferable as a bulk pharmaceutical.

Solution to Problem

To search for a novel salt form of compound A, the present inventors have conducted diligent studies on various salt forms other than the hydrochloride and p-toluenesulfonate monohydrate, and consequently completed the present invention by finding that the tartrate of compound A (hereinafter, also referred to as compound I), particularly, the (+)-tartrate monohydrate of compound A (hereinafter, also referred to as compound II), is useful as a bulk pharmaceutical, without problems in terms of moisture absorption and desorption characteristics, solubility, crystal stability, and chemical stability, compared with various other salts.

The present invention relates to:

[1] $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide tartrate;

[2] $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide(+)-tartrate monohydrate;

[3] a compound according to [2], which is crystals;

[4] a compound according to [3], which is crystals having characteristic peaks at diffraction angles (2θ) of 14.5, 17.2, 20.4, 21.3, 22.1, and 23.4)(°) by powder X-ray diffraction;

[5] a compound according to [3], which is crystals having characteristic peaks at diffraction angles (2θ) of 13.9, 17.1, 17.7, 18.6, 21.3, 21.8, and 24.3)(°) by powder X-ray diffraction;

[6] a compound according to [3], which is crystals having characteristic peaks at diffraction angles (2θ) of 13.9, 16.9, 17.5, 18.5, 21.4, and 22.1)(°) by powder X-ray diffraction;

[7] a pharmaceutical drug comprising a compound according to any one of [1] to [6] as an active ingredient; and

[8] an activated blood coagulation factor X inhibitor comprising a compound according to any one of [1] to [6] as an active ingredient.

In the present specification, "crystal" refers to a solid whose internal structure is composed of constituent atoms (or groups of atoms) three-dimensionally arranged in an ordered repeating pattern, and is distinguished from amorphous solids free from such an ordered internal structure.

In the present specification, "salt" also encompasses salts of solvate forms, for example, salts of hydrate forms, unless otherwise specified.

In the present specification, "tartaric acid" means either (+)-tartaric acid or (−)-tartaric acid, or both, unless otherwise specified.

In the present specification, "aqueous solvent" refers to a mixed solvent of water and a solvent other than water. For example, a mixed solvent of water and ethanol is also referred to as aqueous ethanol, and a mixed solvent of water and isopropyl alcohol is also referred to as aqueous isopropyl alcohol.

In the present specification, "%" used in the "% aqueous solvent" represents the proportion of water to the mixed solvent of water and solvent other than water. For example, aqueous ethanol having a water proportion of 20% is also referred to as 20% aqueous ethanol.

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (A):

[Formula 2]

(A)

is identified by the International Nonproprietary Name (INN) of edoxaban (N-(5-chloropyridin-2-yl)-N'-[(1S,2R,4S)-4-(N,N-dimethylcarbamoyl)-2-(5-methyl-4,5,6,7-tetrahydro[1,3]thiazolo[5,4-c]pyridine-2-carboxamido)cyclohexyl]oxamide).

Compound A can be produced according to a method described in Patent Literature 1 to 8 or a method equivalent thereto.

The (+)-tartrate monohydrate of compound A (compound II) can be obtained, for example, by adding an equimolar amount of a solution of (+)-tartaric acid in ethanol to compound A.

The crystals of compound II of the present invention can be produced, for example, by dissolving compound II in an appropriate solvent, performing pH adjustment, solution concentration, and so on, and bringing compound II to a supersaturated state for deposition.

The deposition of the crystals may be initiated spontaneously in a reaction vessel, and can also be initiated or promoted by inoculating seed crystals, or providing ultrasonic stimulation or mechanical stimulation such as the scrubbing of the reactor surface.

The temperature to crystallize compound II into crystals is preferably 0° C. to 40° C., more preferably 20° C. to 30° C.

The deposited crystal can be isolated by, for example, filtration, centrifugation, or decantation. The isolated crystals can be washed, if necessary, with an appropriate solvent.

Examples of the solvent for washing the crystals of compound II include water, ethanol, isopropanol, acetone, ethyl acetate, toluene, acetonitrile, methyl acetate, and ether. The solvent is preferably ethanol.

The isolated crystals can be dried, usually at a temperature of 10° C. to 100° C., preferably 30° C. to 50° C., until the weight becomes almost constant. The drying of the crystals can also be performed, if necessary, in the presence of a desiccant such as silica gel or calcium chloride, or under reduced pressure.

The dried crystals may be allowed to absorb moisture usually at a temperature of 10° C. to 30° C. and at 20% to 90% relative humidity, preferably at a temperature of 20° C. to 30° C. and at 50% to 80% relative humidity, until the weight becomes almost constant.

The obtained crystals can be recrystallized or slurry-purified, to improve their purity and quality.

The recrystallization of compound II of the present invention is achieved by a method usually used in the field of organic synthetic chemistry. Specifically, examples of the solvent used in the recrystallization of compound II of the present invention include water, methanol, ethanol, acetone, aqueous methanol, aqueous ethanol, aqueous 2-propanol, aqueous acetone, and aqueous acetonitrile. The solvent is preferably aqueous methanol, aqueous ethanol, aqueous 2-propanol, aqueous acetone, or aqueous acetonitrile.

Slurry purification is the procedure of suspending crystals of the compound in an appropriate solvent, stirring the suspension, and then isolating the crystals again. Examples of the solvent used in the slurry purification of compound II of the present invention include water, methanol, ethanol, 2-propanol, acetone, acetonitrile, methylene chloride, toluene, methyl acetate, ethyl acetate, pentane, tetrahydrofuran, N,N-dimethylformamide, water, hexane, diisopropyl ether, ether, aqueous ethanol, aqueous 2-propanol, and aqueous acetone. The solvent is preferably water, methanol, ethanol, 2-propanol, acetone, acetonitrile, ethyl acetate, pentane, aqueous ethanol, aqueous 2-propanol, or aqueous acetone.

Figure 1:
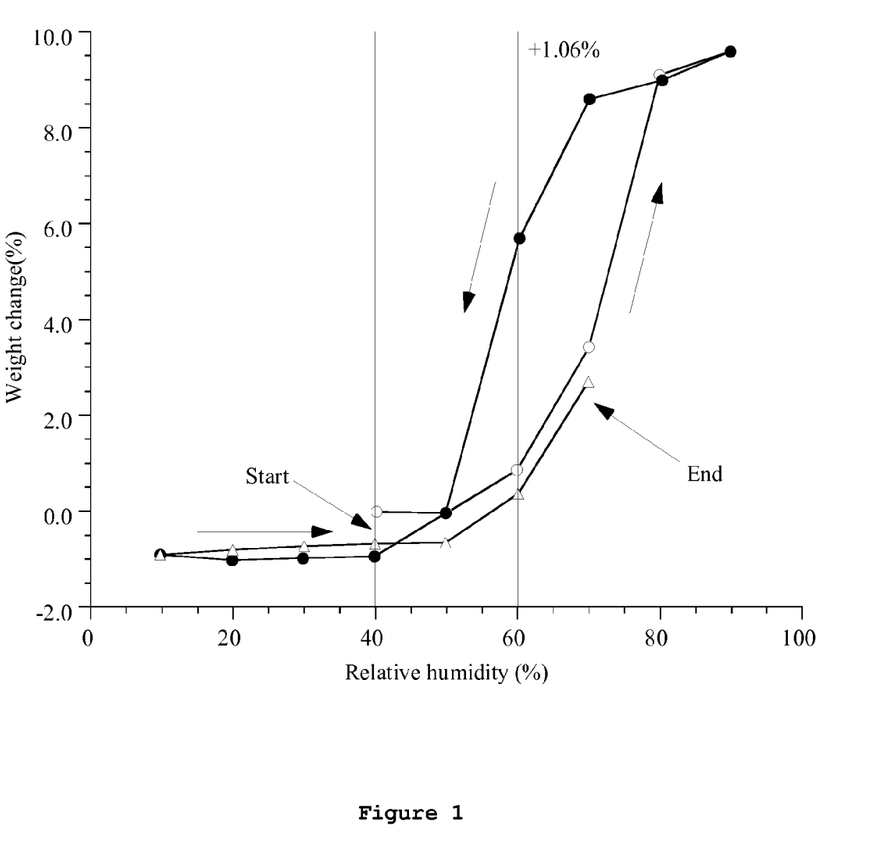
FIG. 1 is a diagram showing the moisture absorption and desorption characteristics of the hydrobromide of compound A. The vertical axis shows weight change (%), and the horizontal axis shows relative humidity (%). The numeric value (%) in the upper central part of the diagram denotes weight change (%) between 40 and 60% relative humidities.
Figure 2:
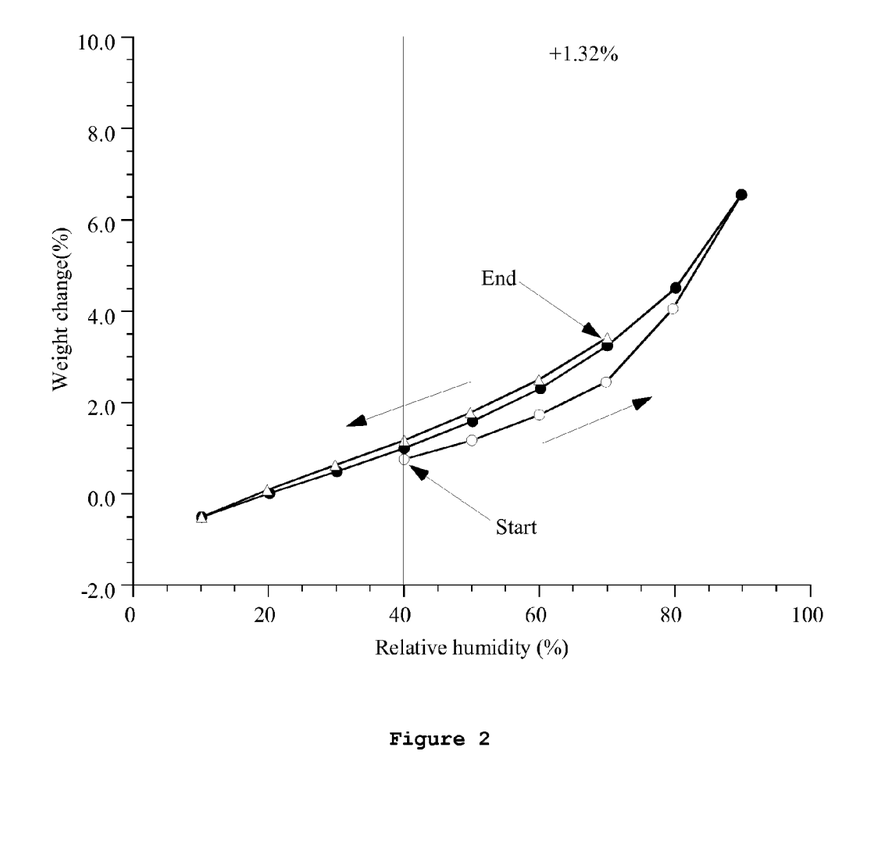
FIG. 2 is a diagram showing the moisture absorption and desorption characteristics of the hemisulfate of compound A. The vertical axis shows weight change (%), and the horizontal axis shows relative humidity (%). The numeric value (%) in the upper central part of the diagram denotes weight change (%) between 40 and 60% relative humidities.
Figure 3:
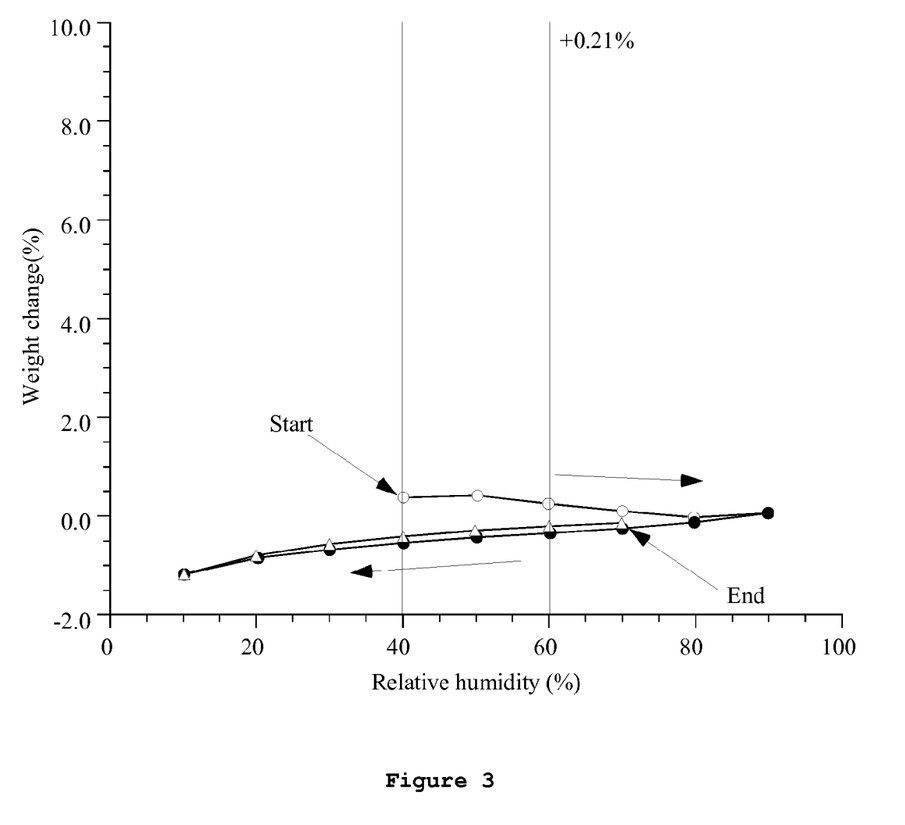
FIG. 3 is a diagram showing the moisture absorption and desorption characteristics of the benzenesulfonate of compound A. The vertical axis shows weight change (%), and the horizontal axis shows relative humidity (%). The numeric value (%) in the upper central part of the diagram denotes weight change (%) between 40 and 60% relative humidities.
Figure 4:
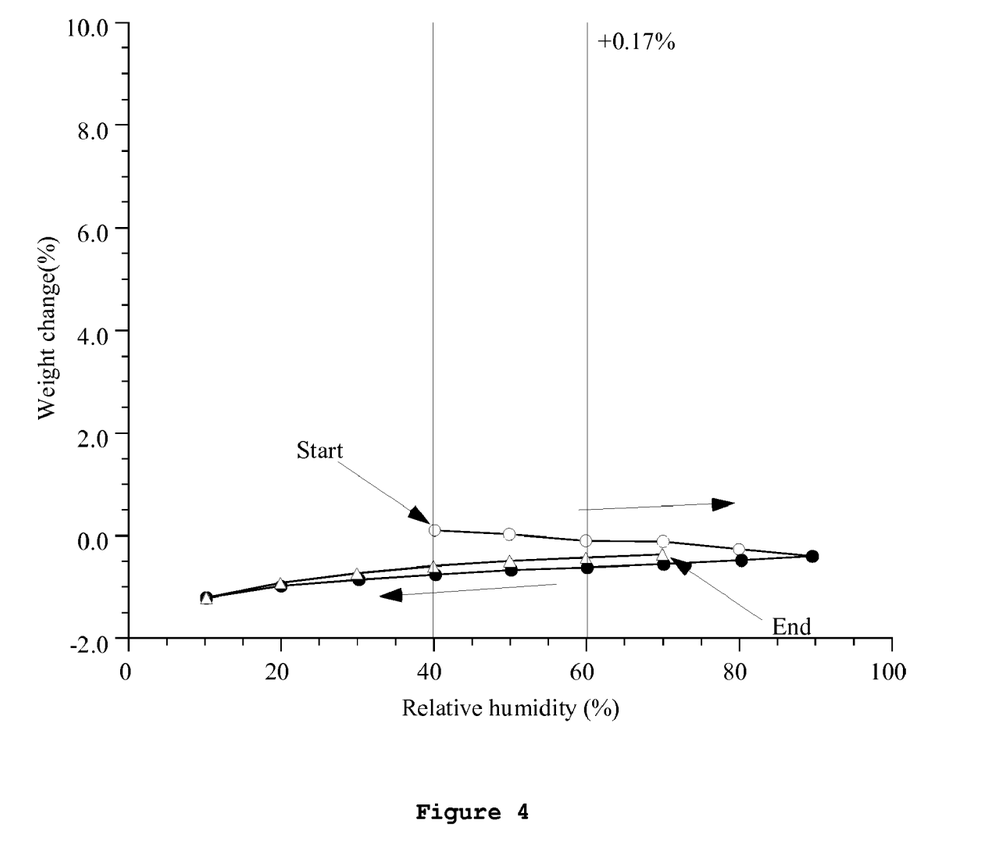
FIG. 4 is a diagram showing the moisture absorption and desorption characteristics of the citrate of compound A. The vertical axis shows weight change (%), and the horizontal axis shows relative humidity (%). The numeric value (%) in the upper central part of the diagram denotes weight change (%) between 40 and 60% relative humidities.
Figure 5:
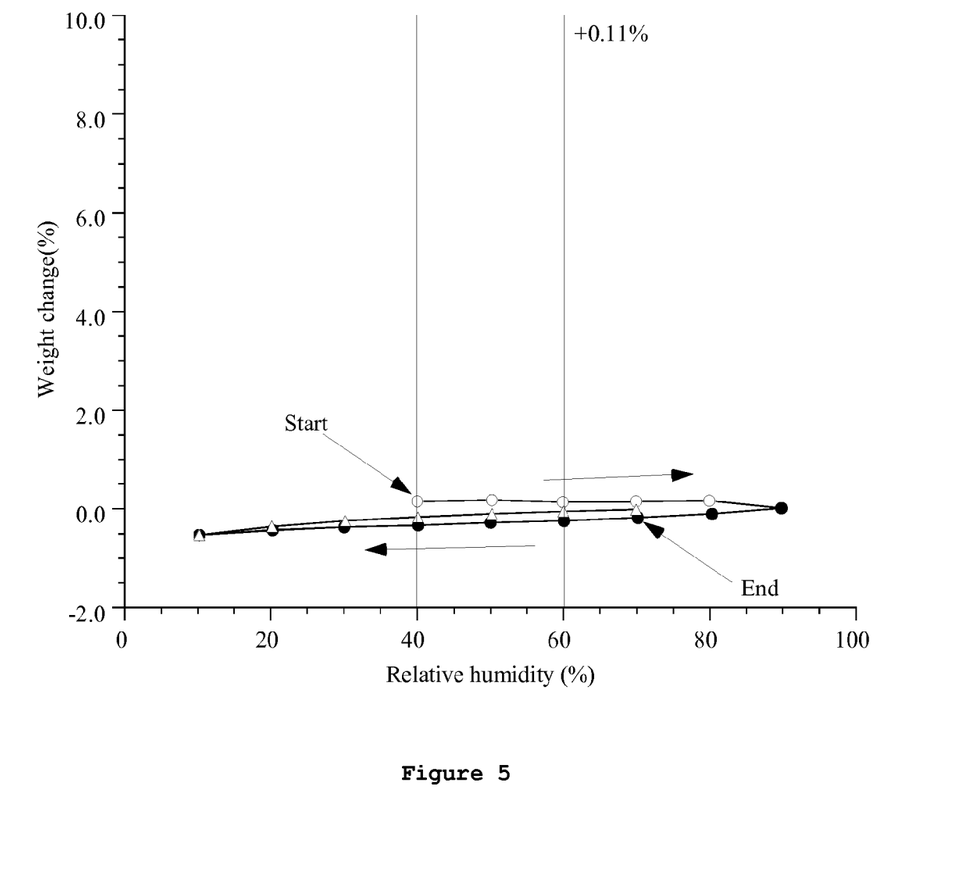
FIG. 5 is a diagram showing the moisture absorption and desorption characteristics of the (+)-tartrate of compound A. The vertical axis shows weight change (%), and the horizontal axis shows relative humidity (%). The numeric value (%) in the upper central part of the diagram denotes weight change (%) between 40 and 60% relative humidities.
Figure 6:
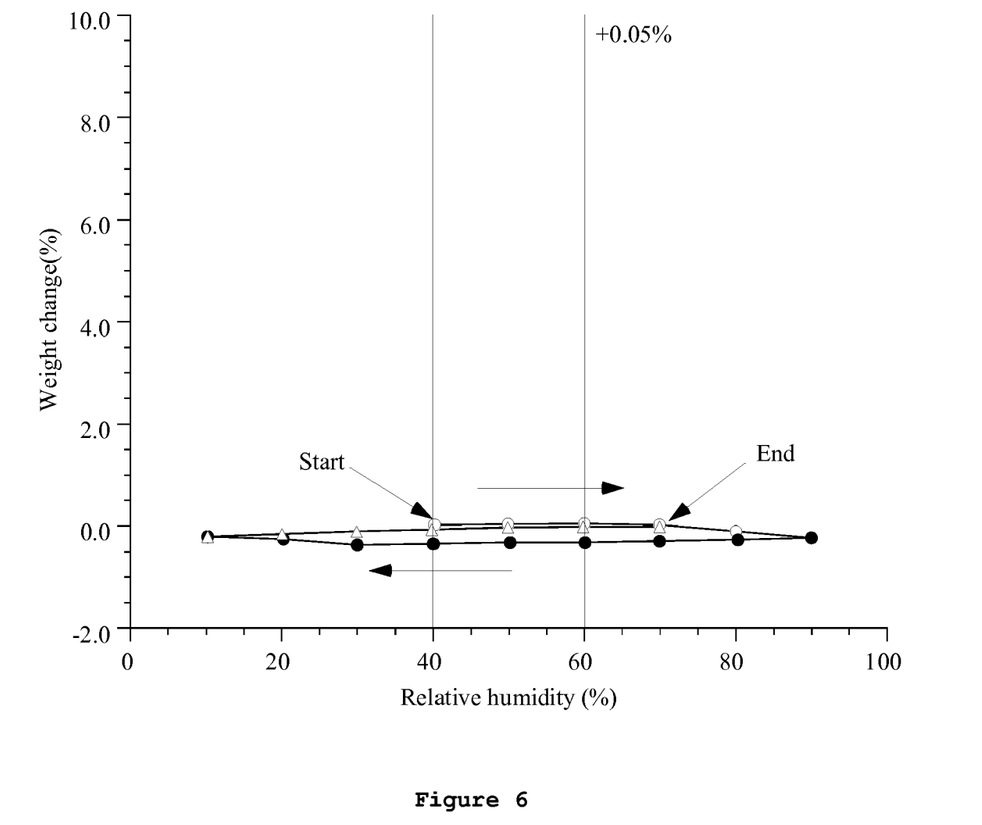
FIG. 6 is a diagram showing the moisture absorption and desorption characteristics of the free form of compound A. The vertical axis shows weight change (%), and the horizontal axis shows relative humidity (%). The numeric value (%) in the upper central part of the diagram denotes weight change (%) between 40 and 60% relative humidities.
Figure 7:
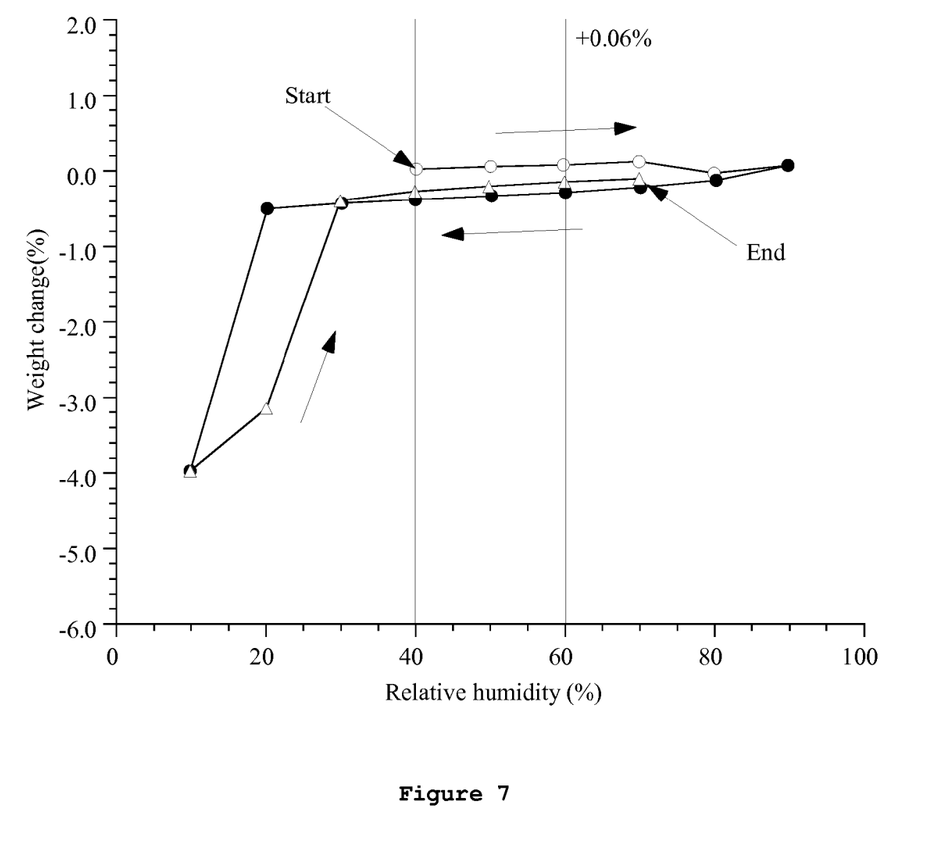
FIG. 7 is a diagram showing the moisture absorption and desorption characteristics of the nitrate of compound A. The vertical axis shows weight change (%), and the horizontal axis shows relative humidity (%). The numeric value (%) in the upper central part of the diagram denotes weight change (%) between 40 and 60% relative humidities.
Figure 8:
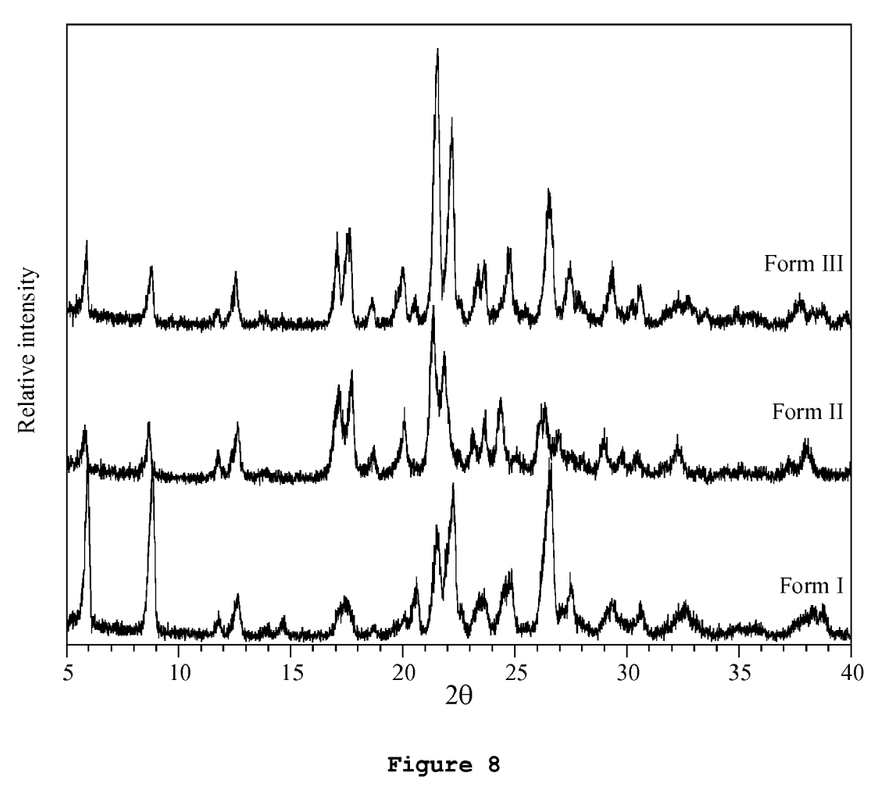
FIG. 8 is a diagram showing the powder X-ray diffraction of the (+)-tartrate (Form I, Form II, and Form III) of compound A. The vertical axis shows relative intensity, and the horizontal axis shows diffraction angles (2θ).

Compound II forms crystalline polymorphs (Forms I, II, and III) in the recrystallization, as described later. Moreover, compound II also forms crystalline polymorphs (Forms II and III) in the slurry purification. Form I has characteristic peaks at diffraction angles (2θ) of 14.5, 17.2, 20.4, 21.3, 22.1, and 23.4)(°) by powder X-ray diffraction (Form I of FIG. 8). Form II has characteristic peaks at diffraction angles (2θ) of 13.9, 17.1, 17.7, 18.6, 21.3, 21.8, and 24.3)(°) by powder X-ray diffraction (Form II of FIG. 8). Form III has characteristic peaks at diffraction angles (2θ) of 13.9, 16.9, 17.5, 18.5, 21.4, and 22.1)(°) by powder X-ray diffraction (Form III of FIG. 8).

The crystals of compound II thus obtained were highly soluble in water compared with compound A, as described later.

Moreover, when the crystals of compound II were stored for 4 days under three standard relative humidity conditions at 25° C., they were stable without change both in weight and in crystal form. On the other hand, crystals of the hydrobromide of compound A exhibited a great increase in weight.

Furthermore, the moisture absorption and desorption characteristics of the crystals of compound II were studied and used as an index for long-term storage stability. As a result, the crystals of compound II had 1% or less weight change at 40% to 60% relative humidity, and exhibited favorable moisture absorption and desorption characteristics.

A pharmaceutical drug comprising the salt and/or crystals of the present invention as an active ingredient is preferably provided in the form of a pharmaceutical composition comprising the salt and/or crystals of the present invention as an active ingredient and one or two or more pharmaceutical additives. The dosage form of the pharmaceutical drug of the present invention is not particularly limited, and it can be administered orally or parenterally, and is preferably administered orally.

The salt and/or crystals of the present invention exhibits a high inhibitory effect on activated blood coagulation factor X (FXa), and is thus useful as an anticoagulant agent or as a preventive and/or therapeutic agent for thrombosis or embolism. The pharmaceutical composition of the present invention is useful as a pharmaceutical drug for mammals including humans, as an activated blood coagulation factor Xa inhibitor, as an anticoagulant agent, as a preventive and/or therapeutic agent for thrombosis or embolism, as a preventive and/or therapeutic agent for thrombotic diseases, for example, as a preventive (in the present specification, prevention encompasses secondary prevention) and/or therapeutic agent for cerebral infarction, cerebral embolism, myocardial infarction, angina pectoris, unstable angina, acute coronary syndrome (ACS), pulmonary infarction, pulmonary embolism, thromboembolism or seizure accompanying nonvalvular atrial fibrillation (NVAF), deep vein thrombosis, disseminated intravascular coagulation syndrome, thrombosis after prosthetic valve/joint replacement, thromboembolism after total hip replacement (THR), thrombosis and reocclusion after revascularization, thrombosis at the time of extracorporeal circulation, blood coagulation at the time of blood collection, Buerger's disease, thromboembolism accompanying systemic inflammatory response syndrome (SIRS), or thromboembolism accompanying multiple organ dysfunction syndrome (MODS), or as a bulk pharmaceutical for these preventive and/or therapeutic agents. The pharmaceutical drug comprising the salt and/or crystals of the present invention is also useful in terms of no necessity for concern about the possibility of sulfonic acid ester formation.

Examples of pharmacologically or pharmaceutically acceptable additives used in the production of the pharmaceutical composition can include, but are not limited to, excipients, disintegrants or disintegration aids, binders, lubricants, coating agents, pigments, diluents, bases, solubilizers or solubilization aids, tonicity agents, pH adjusters, stabilizers, propellants, and adhesives.

Examples of preparations suitable for oral administration can include tablets, powders, granules, and capsules. Moreover, examples of preparations suitable for parenteral administration can include injections, drops, suppositories, inhalants, and patches. Of these, capsules or tablets or the like are preferable.

The dose of the pharmaceutical drug of the present invention is not particularly limited, and can be selected appropriately according to various conditions such as the age, body weight, and conditions of a patient. It is preferred to administer the pharmaceutical drug of the present invention at a dose of 1 mg to 1000 mg, preferably 5 mg to 500 mg, more preferably 5 mg to 300 mg, even more preferably 5 mg to 100 mg of the active ingredient per day in an adult human, which is administered in one portion or in several portions, preferably in one portion or in two portions, per day, according to the conditions.

ADVANTAGEOUS EFFECTS OF INVENTION

Compound II of the present invention exhibits favorable crystallinity, and is useful as a bulk pharmaceutical without problems in terms of moisture absorption and desorption characteristics, solubility, crystal stability, and chemical stability, compared with various other salts.

DETAILED DESCRIPTION

Hereinafter, Examples will be described. However, the present invention is not intended to be limited to them.

EXAMPLES

In the present Examples, the measurements of powder X-ray diffraction, thermal analysis (TG/DTA), and elemental analysis were performed under the following conditions.

Measurement conditions of powder X-ray diffraction (radiation source: Cu-Kα rays, filter: Ni, detector: scintillation counter, tube voltage: 35 kV, tube current: 20 mA, scanning rate: 0.025° 2θ/s, scanning range: 2θ=5°-40°, apparatus: Phillips X'Pert-MPD PW 3050)

Measurement conditions of thermal analysis (TG/DTA) (heating rate: 10° C./min., sample container: aluminum pan, reference material: vacant aluminum pan, atmosphere: 200 mL of nitrogen gas/min., sample volume: approximately 5 mg, apparatus: SEIKO Instruments Inc. SSC5200 TG/DTA 220)

Measurement conditions of elemental analysis (sample volume: approximately 2 mg, apparatus: CHNS analysis, type CHNS-932 elementary microanalyzer manufactured by LECO Corp., Cl analysis, COM-980win automatic titrator manufactured by Hiranuma Sangyo Corp.)

Reference Example

Compound A was synthesized according to a method described in Patent Literature 1 to 8.

Example 1

Salt Formation of Compound A and Evaluation of Crystallinity (1) Synthesis of (+)-tartrate monohydrate of compound A (Form I)

409 mg of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (compound A) was dissolved in 20 mL of methylene chloride, and then an equimolar amount of a solution of (+)-tartaric acid in ethanol was added thereto. The solvent was distilled off to obtain a dry solid. To the dry solid, 31 mL of 30% aqueous ethanol was added, and the mixture was dissolved with heating and then left at room temperature. The deposited material was suction-filtered and then dried in air at room temperature to obtain the compound of interest (378 mg, yield: 71%). Form I was confirmed by powder X-ray diffraction.

Theoretical (in terms of monotartrate monohydrate): C, 46.96%; H, 5.35%; N, 13.69%; Cl, 4.95%; S, 4.48%.

Found: C, 46.80%; H, 5.11%; N, 13.73%; Cl, 5.08%; S 4.64%.

Form I had the following characteristic diffraction peaks in powder X-ray diffraction: 2θ=14.5, 17.2, 20.4, 21.3, 22.1, and 23.4°.

(2) Synthesis of (+)-tartrate monohydrate of compound A (Form II): Form II of the (+)-tartrate monohydrate of compound A was obtained in the same way as the synthesis of Form I in paragraph (1) except that 50% aqueous 2-propanol was added to the dried form.

Form II had the following characteristic diffraction peaks in powder X-ray diffraction: 2θ=13.9, 17.1, 17.7, 18.6, 21.3, 21.8, and 24.3°.

(3) Synthesis of (+)-tartrate monohydrate of compound A (Form III): Form III of the (+)-tartrate monohydrate of compound A was obtained in the same way as the synthesis of Form I in paragraph (1) except that 50% aqueous ethanol was added to the dried form.

Form III had the following characteristic diffraction peaks in powder X-ray diffraction: 2θ=13.9, 16.9, 17.5, 18.5, 21.4, and 22.1°.

(4) Salt formation of compound A was attempted using hydrobromic acid, sulfuric acid, methanesulfonic acid, benzenesulfonic acid, phosphoric acid, acetic acid, salicylic acid, maleic acid, lactic acid, malonic acid, succinic acid, citric acid, (−)-malic acid, and nitric acid, in addition to tartaric acid. Various salt formations were performed in the same way as the salt formation using tartaric acid.

As a result, the tartrate, hydrobromide, sulfate, methanesulfonate, benzenesulfonate, phosphate, citrate, and nitrate exhibited diffraction peaks in powder X-ray diffraction and were confirmed to be crystalline powders.

Example 2

Evaluation of Moisture Absorption and Desorption Characteristics

Various samples prepared in Example 1 were separately placed in quartz holders and measured for their moisture absorption and desorption behavior under the following conditions using a microbalance.

Moisture absorption and desorption behavior measurement conditions (sample volume: approximately 20 mg, measurement range: 10-90% RH, measurement temperature: 25° C., variable: within 0.03%, varying length of time: 10 min., apparatus: VTI atmospheric pressure-type automatic water vapor adsorption apparatus SGA-100)

The results are shown in FIGS. 1 to 7.

Compound A and the benzenesulfonate, citrate, nitrate, and tartrate of compound A had 1% or less weight change at 40% to 60% relative humidity. On the other hand, the hydrobromide of compound A exhibited generally favorable moisture absorption and desorption behavior, although its weight change exceeded 1%.

Example 3

Evaluation of Solubility

Solubility was evaluated as follows using various samples prepared in Example 1. A supersaturated amount of each sample was placed in a 12-mL test tube, and 3 mL of a test solution (water, Japanese Pharmacopoeia disintegration test solution No. 1 (JP1), and Japanese Pharmacopoeia disintegration test solution No. 2 (JP2)) was added thereto. The test tube was incubated in a constant-temperature water bath at 37° C. The test tube was shaken using a vortex mixer for 30 seconds every 5 minutes. 30 minutes later, the supernatant was filtered through a membrane filter (pore size: 0.45 μm), appropriately diluted with eluent, and then analyzed by HPLC under the following conditions. The concentration was calculated from a calibration curve prepared before measurement.

Measurement conditions of HPLC (column: Waters Symmetry C18 4.6 mm×150 mm, eluent: 0.05 M phosphate buffer (pH 5.0): acetonitrile=70:30, flow rate: 1 mL/min., detection: UV 220 nm, column temperature: 40° C.)

The results are shown in Table 1.

TABLE 1

|  | Water (Solubility (μg/mL)) | JP1 (Solubility (μg/mL)) | JP2 (Solubility (μg/mL)) |
| --- | --- | --- | --- |
| Hydrobromide of compound A | >2000 | >2000 | 99.2 |
| (+)-Tartrate monohydrate of compound A | >2000 | >2000 | 138 |
| Compound A | 47.5 | >2000 | 49.8 |

Example 4

Evaluation of Crystal Stability

Approximately 50 mg of each of various samples prepared in Example 1 was placed in a weighing bottle and stored at 25° C. in a desiccator whose relative humidity was adjusted to 0%, 52%, or 93% by a saturated salt solution method (silica gel, $Mg(NO_3)_2$, $KNO_3$). After 3-day storage, the weight change was measured, and then the measurements of powder X-ray diffraction and thermal analysis (TG/DTA) were performed.

The results are shown in Table 2.

TABLE 2

| | 0% RH | | 52% RH | | 93% RH | |
|---|---|---|---|---|---|---|
| | Crystal form | Weight change (%) | Crystal form | Weight change (%) | Crystal form | Weight change (%) |
| Hydrobromide of compound A | No change | −0.14 | No change | −0.13 | No change | 10.22 |
| (+)-Tartrate monohydrate of compound A | No change | −0.35 | No change | 0.05 | No change | 0.31 |
| Compound A | No change | −0.32 | No change | −0.22 | No change | −0.04 |

Example 5

Evaluation of Chemical Stability

Approximately 2 mg of each of various samples prepared in Example 1 was weighed into an aluminum pan for thermal analysis and stored under dry heat (50° C., 0% RH) or wet heat (40° C., 75% RH) conditions. 1 week or 2 weeks later, each sample was collected, and the weight change was measured. Then, the whole amount was dissolved in 20 mL of eluent and analyzed by HPLC. For photolysis samples, approximately 10 mg of each sample was weighed into a weighing bottle and stored at 25° C. in a light irradiator. After irradiation at 600,000 or 1,200,000 Lx/hr, the sample was collected, and the weight change was measured. Then, the whole amount was dissolved in 100 mL of eluent and analyzed by HPLC. The residue proportion was determined from the ratio between the concentration of the sample solution calculated from a calibration curve prepared before measurement and the theoretical concentration calculated from weight measurement.

Measurement conditions of HPLC (column: Waters Symmetry C18 4.6 mm×150 mm, eluent: 0.05 M phosphate buffer (pH 5.0): acetonitrile=80:20, flow rate: 1 mL/min., detection: UV 220 nm, column temperature: 40° C.)

The results are shown in Table 3.

TABLE 3

| | Residue (%, mean ± SD) | | | | | | |
|---|---|---|---|---|---|---|---|
| | 50° C., 0% RH | | 40° C., 75% RH | | Light irradiation | | |
| | 1 week later | 2 week later | 1 week later | 2 week later | (Lx · hr) | | |
| | | | | | $60 \times 10^4$ | $120 \times 10^4$ | Color |
| (+)-Tartrate monohydrate of compound A | 100.4 ± 0.7 | 100.1 ± 0.7 | 100.1 ± 0.7 | 100.1 ± 0.3 | 98.2 ± 0.9 | 95.0 ± 1.2 | Slightly changed |
| Compound A | 99.3 ± 0.4 | 97.5 ± 0.7 | 99.8 ± 0.3 | 98.7 ± 1.3 | 92.0 ± 0.3 | 82.8 ± 0.4 | Changed | the crystal having characteristic peaks at diffraction angles (2θ) of 14.5, 17.2, 20.4, 21.3, 22.1, and 23.4 (°) by powder X-ray diffraction.

2. A crystal of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (+)-tartrate monohydrate, the crystal having characteristic peaks at diffraction angles (2θ) of 13.9, 17.1, 17.7, 18.6, 21.3, 21.8, and 24.3 (°) by powder X-ray diffraction.

3. A crystal of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (+)-tartrate monohydrate, the crystal having characteristic peaks at diffraction angles (2θ) of 13.9, 16.9, 17.5, 18.5, 21.4, and 22.1 (°) by powder X-ray diffraction.

4. A pharmaceutical composition comprising the compound according to claim 1 as an active ingredient.

5. A method for treating thrombosis or embolism comprising administering a pharmacologically effective amount of the compound according to one of claim 1, 2 or 3 to a warm-blooded animal.

6. A method for treating cerebral infarction, cerebral embolism, myocardial infarction, angina pectoris, unstable angina, acute coronary syndrome (ACS), pulmonary infarction, pulmonary embolism, thromboembolism or seizure accompanying nonvalvular atrial fibrillation (NVAF), deep vein thrombosis, disseminated intravascular coagulation syndrome, thrombosis after prosthetic valve/joint replacement, thromboembolism after total hip replacement (THR), thrombosis and reocclusion after revascularization, thrombosis at the time of extracorporeal circulation, blood coagulation at the time of blood collection, Buerger's disease, thromboembolism accompanying systemic inflammatory response syndrome (SIRS), or thromboembolism accompanying multiple organ dysfunction syndrome (MODS) comprising administering a pharmacologically effective amount of the compound

The invention claimed is:

1. A crystal of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (+)-tartrate monohydrate, according to one of claims 1, 2 or 3 to a warm-blooded animal.

7. A pharmaceutical composition comprising the crystal according to claim 2 as an active ingredient.

8. A pharmaceutical composition comprising the crystal according to claim 3 as an active ingredient.

9. A method for inhibiting coagulation factor X in a human, comprising administering a pharmacologically acceptable amount of the pharmaceutical composition of claim 1 to the human.

10. A method for inhibiting coagulation factor X in a human, comprising administering a pharmacologically acceptable amount of the pharmaceutical composition of claim 2 to the human.

11. A method for inhibiting coagulation factor X in a human, comprising administering a pharmacologically acceptable amount of the pharmaceutical composition of claim 3 to the human.

12. The method of claim 5, wherein the warm-blooded animal is a human.

* * * * *